US00PP07769P

United States Patent [19]

Saville

[11] Patent Number: Plant 7,769

[45] Date of Patent: Jan. 21, 1992

[54] MINIATURE ROSE PLANT NAMED SAVAPIE

[75] Inventor: F. Harmon Saville, Rowley, Mass.

[73] Assignee: Nor'East Miniature Roses, Inc., Rowley, Mass.

[21] Appl. No.: 591,555

[22] Filed: Oct. 1, 1990

[51] Int. Cl.[5] ..... A01H 5/00

[52] U.S. Cl. ..... Plt./7

[58] Field of Search ..... Plt. 7, 10

*Primary Examiner*—James R. Feyrer

*Attorney, Agent, or Firm*—Christie, Parker & Hale

[57] ABSTRACT

A new miniature rose plant with red and white bi-colored flowers.

1 Drawing Sheet

SUMMARY OF THE INVENTION

The present invention relates to a new and distinct variety of rose plant of the miniature rose class, which was originated by my crossing as seed parent an unnamed, unpatented seedling of my creation and as pollen parent the rose known as "Party Girl" (U.S. Plant No. 4,598). The varietal denomination of this new rose is "Savapie".

Among the novel characteristics possessed by this new variety which primarily distinguishes it from its parent and all other varieties of which I am aware are its unusual red and white bi-colored flowers.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF THE PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "155B" is plate "155B" of The Royal Horticultural Society Colour Chart.

Parentage: Seedling.

*Seed parent.*—Unnamed seedling.

Pollen parent.—"Party Girl".

Class: Miniature.

The following observations are made of specimens grown under glass in Essex County, Mass., during the month of July.

FLOWER

Blooming habit: Continuous.

A. Bud:

(1) *Size.*—Medium.

(2) *Form.*—Ovate.

(3) *Color.*—As sepals divide, bud color is near 155B edged with near 52A.

(4) *Sepals.*—Medium length, smooth.

(5) *Peduncle.*—Length — about ¾ inch. Aspect — straight. Strength — strong. Color — near 144C.

Bloom:

(1) *Size.*—Average size when fully expanded — about 1 to 1¼ inches.

(2) *Borne* — Singly, one to a stem, and in sprays or 3 to 8 blooms.

(3) *Form — High centered at first; outer petals roll under; some petals quill to points.*

(4) *Petalage.*—Number of petals under normal conditions — about 15 to 18.

(5) *Color.*—After sepals fall and as petals begin to unfurl, predominant flower coloring is between near 46A to 47A, until white segments of flower petals become visible. As flowers open to one ⅓ to ½ open stage, white coloring, near 155B, appears as washing into petal's red margins. Extent of white penetration toward margin varies but usually stops short of petal edge with about upper ¼ to 1/5 of petals showing distinct white washing into red. Color line demarcation also varies from abrupt to shading.

As flowers open fully, white pedal coloring becomes more distinct and bi-color effect is most noticeable with red appearing as near 53C. As blooms age, red color tends to "blue" and darkens to near 53A. Reverse of petals, initially near 11D edges with 52A, becomes hardly noticeable. Color at point of petal attachment is near 155B.

C. Petals:

(1) *Texture.*—Firm.

(2) *Appearance.—Inside velvety and outside satiny.*

(3) *Form.—Fan shaped, some pointed apices.*

(4) *Arrangement.—Regularly arranged, imbricated.*

(5) *Petaloids in center.*—Few.

(6) *Persistence.*—Drop off cleanly.

(7) *Fragrance.*—Slight.

(8) *Lasting Quality.*—Lasting quality on plant is very long.

REPRODUCTIVE ORGANS

A. Stamens, filaments and anthers:

*Arrangement.*—Regularly arranged around styles.

*Color.*—near 18A.

B. Pollen:

*Color.*—near 18A.

C. Styles: Uneven, relatively long.

D. Stigmas:
*Color.*—near 154C.
E. Hips: None observed.

PLANT

A. Form: Upright, branching.
B. Growth: Very vigorous.
*Height attained.*—*About* 14 to 16 inches.
C. Foliage: Compound 5 to 7 leaflets.
(1) *Size.*—Medium.
(2) *Quantity.*—Abundant.
(3) *Color.*—New foliage: Upper side — near 146A. Under side — near 146B. Old foliage: Upper side — near 147A. Under side — near 147C.
(4) *Shape.*—Oval, pointed.
(5) *Texture.*—Upper side is semi-glossy; under side is matte.
(6) *Edge.*—Serrate.
(7) *Serration.*—Large.
(8) *Leaf stem.*—*Color* — *near* 183C. Under side — 183D.
(9) *Stipules.*—Medium length, not bearded.

(10) *Resistance to Disease.*—Blackspot — Average. Mildew — Average. Rust — Average.
D. Wood:
(1) *New Wood.*—Color — near 138B. Bark — smooth.
(2) *Old wood.*—Color — near 146B. Bark — smooth.
E. Thorns:
*Quantity (main stalk).*—*very few.*
*On laterals from stalk.*—*few.*
*Form.*—Long, thin, straight point.
*Length.*—medium.
*Color.*—near 200D.
*Position.*—irregular.
*Prickles.*—None.
F. Winter Hardiness: Needs protection in severe climates.

I claim:
1. A new and distinct variety of rose plant of the miniature rose class, substantially as shown and described, characterized particularly by attractive red and white bi-colored flowers.

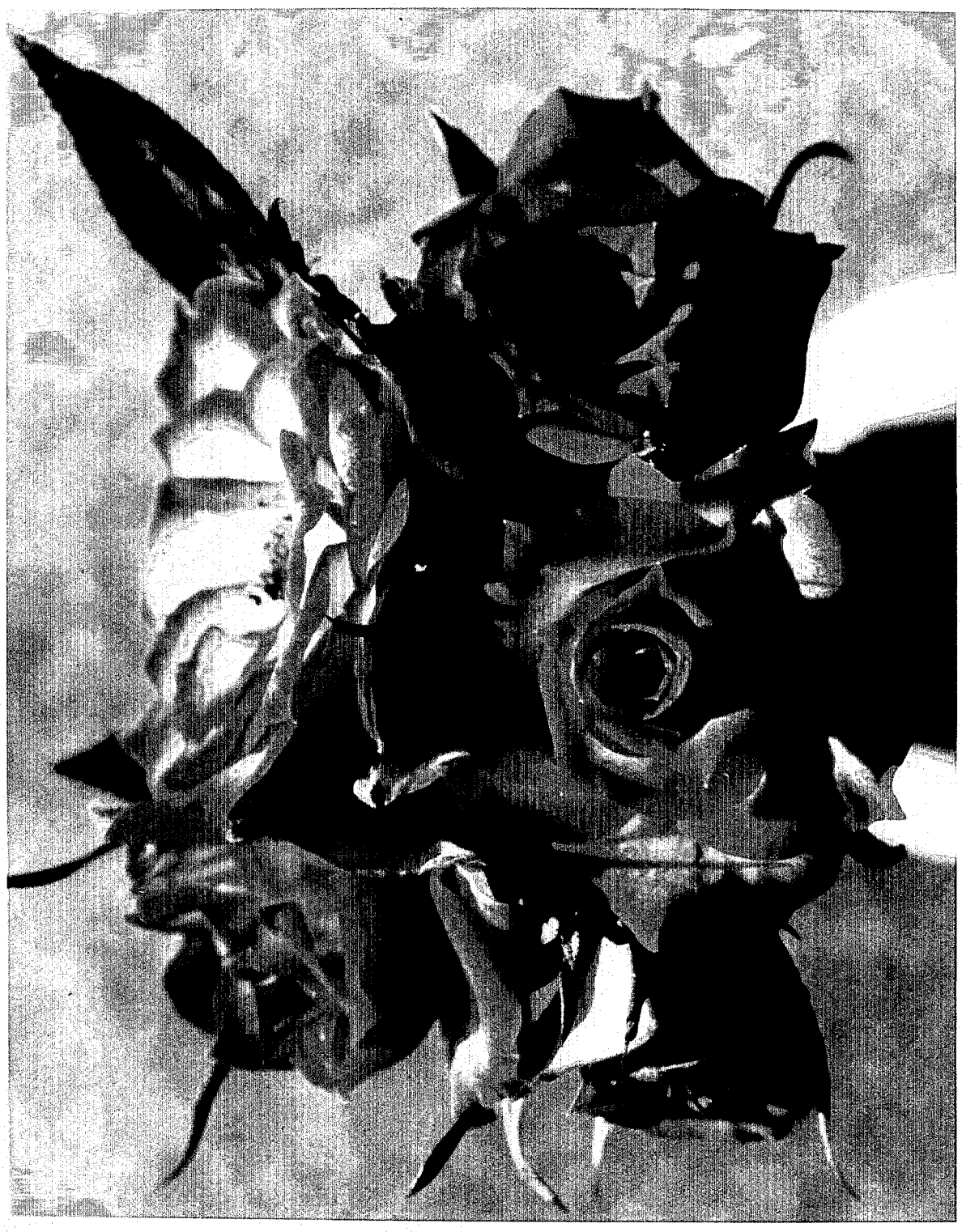

* * * * *